United States Patent [19]

Prutchi

[11] Patent Number: 6,022,322
[45] Date of Patent: Feb. 8, 2000

[54] NON-INVASIVE CARDIORESPIRATORY MONITOR WITH SYNCHRONIZED BIOIMPEDANCE SENSING

[75] Inventor: David Prutchi, Lake Jackson, Tex.

[73] Assignee: Intermedics Inc., Angleton, Tex.

[21] Appl. No.: 09/020,277

[22] Filed: Feb. 6, 1998

[51] Int. Cl.⁷ ................................................. A61N 5/00
[52] U.S. Cl. ..................... 600/506; 600/533; 600/536; 607/27; 607/32
[58] Field of Search ..................... 600/528–538, 600/500–509, 300, 481; 607/32, 27, 60, 62, 28, 20; 128/903, 904

[56] References Cited

U.S. PATENT DOCUMENTS

| | | | |
|---|---|---|---|
| 3,316,896 | 5/1967 | Thomasset | 128/2.1 |
| 4,450,527 | 5/1984 | Sramek | 364/415 |
| 5,109,863 | 5/1992 | Semmlow et al. | 128/715 |
| 5,178,154 | 1/1993 | Ackmann | 128/713 |
| 5,324,315 | 6/1994 | Grevious | 607/60 |
| 5,354,319 | 10/1994 | Wyborny et al. | 128/904 |
| 5,423,326 | 6/1995 | Wang et al. | 128/713 |
| 5,443,073 | 8/1995 | Wang et al. | 128/713 |
| 5,469,859 | 11/1995 | Tsoglin et al. | 128/723 |
| 5,503,157 | 4/1996 | Sramek | 600/506 |
| 5,505,209 | 4/1996 | Reining | 128/734 |
| 5,876,353 | 3/1999 | Riff | 600/529 |

*Primary Examiner*—Cary O'Connor
*Assistant Examiner*—Michael Astorino
*Attorney, Agent, or Firm*—Schwegman, Lundberg, Woessner & Kluth

[57] ABSTRACT

A cardiorespiratory monitor that generates bioimpedance sensing signals that produce substantially no interference with bioimpedance signals generated by implanted devices. The monitor detects the bioimpedance signal generated by the implanted device, using a voltage detector or a telemetry circuit, for example. The monitor analyzes this detected signal to generate a bioimpedance sensing signal that will not interfere with the sensed signal. For instance, if the monitor produces a pulsed sensing signal, the pulses are delivered in an interval of the detected signal where no pulses are present. Similarly, if the monitor produces a high frequency AC sensing signal, the zero crossings of the AC sensing signal are positioned during the delivery of a pulse by the implanted device.

32 Claims, 3 Drawing Sheets

NON-INVASIVE CARDIORESPIRATORY MONITOR WITH SYNCHRONIZED BIOIMPEDANCE SENSING

BACKGROUND OF THE INVENTION

1. Field of the Invention

The present invention generally relates to methods and apparatus for generating an impedance cardiogram and, more particularly, to methods and apparatus for generating an impedance cardiogram for patients having cardiac stimulators which include bioimpedance sensors, as well as methods and apparatus for calibrating cardiac stimulators which include bioimpedance sensors.

2. Background of the Related Art

For a variety of reasons, a person's heart may not function properly and, thus, endanger the person's well-being. Medical devices have been developed to assist physicians in the diagnosis and treatment of cardiac dysfunction. In regard to the diagnosis of cardiac dysfunction, it has been found that the volume of blood that a person's heart is able to pump, commonly referred to as "cardiac output," is one of the most important cardiovascular parameters. The cardiac output reflects the supply of oxygen and nutrients to the body. Measurements of cardiac output provide information for quantifying the extent of cardiac dysfunction and for indicating the optimal course of treatment.

Both invasive and non-invasive instruments are available for measuring a person's cardiac output. The invasive techniques for measuring cardiac output require complex instrumentation, which must be operated by skilled personnel, and involve the penetration of the skin by a catheter. Due to the various disadvantages of invasive techniques, non-invasive techniques are generally preferred in the majority of cases.

Although a variety of non-invasive techniques exist, one of the more popular techniques is referred to as "impedance cardiography." Impedance cardiography is a method of measuring the electrical impedance of the body to determine cardiac output. In impedance cardiography, electrodes are typically connected at two locations on the body. A device, referred to as a cardiorespiratory monitor, generates an electric current that flows through the body from one electrode to the other. A second pair of electrodes, which are positioned between the first pair of electrodes, sense the potential developed by the electrical current as it flows through the body and delivers this sensed potential to the monitor. Based on the sensed potential and the injected current, the monitor calculates the impedance of the body.

In general, the impedance of the portion of the body between the electrodes varies inversely with the amount of blood flowing through the vessels in that region. Such impedance is often referred to as "bioimpedance" because it is the impedance of a set of biological tissues. In particular, if the first pair of electrodes are placed such that the current flows through the thorax, i.e., the cavity in which the heart and lungs lie, then the changes in the measured impedance result from changes in the amount of blood pumped by the heart.

The instantaneous amount of blood in the vessels is directly related to the performance of the heart. When blood is pumped out of the heart, the vessels in the thorax become momentarily filled with blood, and the impedance in the thorax rapidly decreases. After the ventricular contraction is complete, the impedance increases to its former level. Analysis of bioimpedance can therefore provide information related to cardiac output. Specifically, to obtain the cardiac output, the stroke volume, which is the amount of blood being ejected during each cardiac cycle, is first computed. The stroke volume may be calculated in a number of different ways, but, generally, it relates to the derivative of the impedance signal. Once the stroke volume has been determined, the cardiac output is computed by multiplying the stroke volume by the heart rate.

However, as anyone familiar with the bioelectrical characteristics of the human body is well aware, a variety of different factors can influence a bioimpedance measurement. For instance, one of the problems encountered in using thoracic impedance to derive the stroke volume is that the thoracic impedance is influenced by the effects of respiration. Similarly, if the patient is moving, during a stress test for instance, the movement also interferes with the thoracic impedance measurement and, thus, the subsequent calculation of stroke volume and cardiac output. Furthermore, when this technique is applied to patients suffering from severe cardiac dysfunction, the measured thoracic impedance may vary markedly from one cycle to another, thus making a qualitative determination of cardiac output difficult to obtain. In view of various problems such as these, a variety of different techniques have been developed for better correlating the measured thoracic impedance to cardiac output by eliminating the influences of these various problematic factors. As a result, impedance cardiography has improved vastly over the past several years and has become an important technique in the detection and treatment of cardiac dysfunction.

Bioimpedance signals are not only useful in the generation of impedance cardiographs using non-invasive monitors as discussed above. For instance, once a person has been diagnosed as having cardiac dysfunction, a physician may determine that a cardiac stimulator may be used to treat the condition. A cardiac stimulator is a medical device that delivers electrical stimulation to a patient's heart. The cardiac stimulator generally includes a pulse generator for creating electrical stimulation pulses and a conductive lead for delivering these electrical stimulation pulses to the designated portion of the heart.

To understand how impedance measurement may be used to enhance the operation of a cardiac stimulator, it is beneficial to understand how cardiac stimulators have evolved. Early pacemakers did not monitor the condition of the heart. Rather, early pacemakers simply provided stimulation pulses at a fixed rate and, thus, kept the heart beating at that fixed rate. However, it was found that pacemakers of this type used an inordinate amount of energy because the stimulation pulses were not always needed. The human heart includes a sinus node located above the atria. The sinus node provides the electrical stimulation that causes a heart to contract. Even the sinus node of a heart in need of a pacemaker often provides such stimulation. Accordingly, if a heart, even for a short period, is able to beat on its own, providing an electrical stimulation pulse using a pacemaker wastes the pacemaker's energy.

To conserve power, pacemakers were subsequently designed to monitor the heart and to provide stimulation pulses only when necessary. These pacemakers were referred to as "demand" pacemakers because they provided stimulation only when the heart demanded stimulation. If a demand pacemaker detected a natural heartbeat within a prescribed period of time, typically referred to as the "escape interval", the pacemaker provided no stimulation pulse. Because monitoring uses much less power than generating stimulation pulses, the demand pacemakers took a large step toward conserving the limited energy contained in the pacemaker's battery.

Clearly, the evolution of the pacemaker did not cease with the advent of monitoring capability. Indeed, the complexity of pacemakers has continued to increase in order to address the physiological needs of patients as well as the efficiency, longevity, and reliability of the pacemaker. For instance, even the early demand pacemakers provided stimulation pulses, when needed, at a fixed rate, such as 70 pulses per minute. To provide a more physiological response, pacemakers having a programmably selectable rate were developed. So long as the heart was beating above this programmably selected rate, the pacemaker did not provide any stimulation pulses. However, if the heart rate fell below this programmably selected rate, the pacemaker sensed the condition and provided stimulation pulses as appropriate.

To provide even further physiological accuracy, pacemakers have now been developed that automatically change the rate at which the pacemaker provides stimulation pulses. These pacemakers are commonly referred to as "rate-responsive" pacemakers. Rate-responsive pacemakers sense a physiological parameter of the patient and alter the rate at which the stimulation pulses are provided to the heart. Typically, this monitored physiological parameter relates to the changing physiological needs of the patient. For instance, when a person is at rest, the person's heart may beat relatively slowly to accommodate the person's physiological needs. Conversely, when a person is exercising, the person's heart tends to beat rather quickly to accommodate the person's heightened physiological needs. Unfortunately, the heart of a person in need of a pacemaker may not be able to beat faster on its own. In fact, prior to the development of rate-responsive pacemakers, patients were typically advised to avoid undue exercise, and pacemaker patients that engaged in exercise tended to tire quickly.

Rate-adaptive pacemakers help relieve this problem by sensing one or more physiological parameters of a patient that indicates whether the heart should be beating slower or faster. If the pacemaker determines that the heart should be beating faster, the pacemaker adjusts its base rate upward to provide a faster pacing rate if the patient's heart is unable to beat faster on its own. Similarly, if the pacemaker determines that the patient's heart should be beating more slowly, the pacemaker adjusts its base rate downward to conserve energy and to conform the patient's heartbeat with the patient's less active state.

One common rate-adaptive sensor measures physical activity as a parameter for rate adaption. Quite commonly, a cardiac stimulator employs an accelerometer, which is a device that responds to a patient movements, to measure the patient's physical activity. One important advantage of a physical-activity sensor is its rapid response to patient activity. For instance, a physical-activity sensor responds favorably to activities which create vibration, such as jogging, walking, and stair climbing. Furthermore, the typical physical-activity sensor is quite simple in that it requires no special leads or implantation procedures.

A physical-activity sensor may possess various disadvantages as well. First, it should be understood that a physical-activity sensor is not generally regarded as a truly physiologic sensor because it does not measure true metabolic demand. For instance, activities such as bicycling may require an increased metabolic demand by the patient, but such activities may not promote rate adaptation because little vibration or few accelerations occur. Furthermore, cardiac stimulators that employ physical activity sensors typically begin rate adaption only when the vibration or accelerations measured by the physical activity sensor exceeds a preprogrammed level. Thus, it is difficult for such a cardiac stimulator to attain a scaled response to gradations of metabolic demand. Also, a physical activity sensor may generate undesirable responses to noise disturbances external to the body, such as vibrations caused by machinery, or from disturbances within the body, such as coughing, sneezing, and laughing.

As can be seen from the above-discussion, physical activity sensors, while exhibiting certain important advantages, do not provide the cardiac stimulator with a true measure of metabolic demand. Accordingly, certain rate-adaptive pacemakers have been developed which employ a metabolic-demand sensor that may be used alone or in conjunction with a physical activity sensor. A metabolic-demand sensor analyzes impedance signals that relate to cardiac performance to adapt the pacing rate to the metabolic demands of the patient. For instance, the pacemaker may analyze impedance measurements to determine the stroke volume of the heart and the minute volume of respiration as indications of the metabolic need of the patient. In normal human subjects with healthy hearts, the stroke volume of the heart has been found to remain relatively constant over a wide range of exertion. Increases in cardiac output required to meet physiologic needs are primarily provided by increasing the heart rate. However, when a patient with a pacemaker begins to exert himself, the heart attempts to increase its stroke volume to meet the increased metabolic needs of the patient. However, the stroke volume cannot increase by a factor of more than about 2 or 2½ times for a typical patient. Thus, changes in stroke volume may be measured to increase the pacing rate to provide the increased cardiac output required by the increased metabolic demand of the patient. In addition to determining stroke volume and minute ventilation, cardiac stimulators may also use impedance sensors to derive similar rate and non-rate parameters from derived cardiac and hemodynamic parameters and, also, to detect and confirm tachyarrhythmias.

Much like the externally attached sensors described above in regard to the non-invasive cardiorespiratory monitor, impedance is measured in implantable devices by establishing an electrical current between two implanted electrodes and measuring the resulting voltage between the same electrodes or between another set of implanted electrodes. As with the external monitors, the current may be applied as a relatively high frequency AC carrier or as periodic narrow pulses. As a general rule, modern implantable cardiac stimulators use pulse-based methods rather than the high-frequency AC carrier methods because the former methods exhibit reduced power consumption in comparison with the latter methods.

Although metabolic-demand sensors of this type enhance the performance of rate adaptive pacemakers, certain difficulties still exist. For instance, the implantable devices use filters and other signal processing means to extract parameters from the impedance signals, and these parameters are believed to be representative of some physiological parameter. However, due to the wide variability between implants, empirical calibration factors are used to relate these estimated parameters to the true metabolic demand of the patient. Unfortunately, because of the interference described below, it is difficult to measure true metabolic demand with current cardiorespiratory monitors that use bioimpedance sensing.

Furthermore, the use of a non-invasive impedance cardiograph technique of a patient having an implanted rate adaptive cardiac stimulator which uses a metabolic demand sensor can create various problems. These problems generally originate because of the great similarity in impedance measurement techniques between the external impedance cardiograph device and the internal impedance-measuring cardiac stimulator. Because each device uses similar signals and similar portions of the elecromagnetic spectrum, simultaneous impedance measurement using both devices results in cross-interference. Such cross-interference may cause the implanted cardiac stimulator to operate in a less than ideal physiologic manner, and it may also cause the impedance cardiograph to generate inaccurate measurements of cardiac output.

The present invention may be applicable to one or more of the problems discussed above.

SUMMARY OF THE INVENTION

Certain aspects commensurate in scope with the originally claimed invention are set forth below. It should be understood that these aspects are presented merely to provide the reader with a brief summary of certain forms the invention might take and that these aspects are not intended to limit the scope of the invention. Indeed, the invention may encompass a variety of aspects that may not be set forth below.

In accordance with one aspect of the present invention, there is provided a cardiorespiratory measurement device that includes means for determining a property of a signal generated by an implanted device, and means for generating a bioimpedance sensing signal correlative to the property that produces substantially no interference with the signal of the implanted device.

In accordance with another aspect of the present invention, there is provided a cardiorespiratory measurement device that includes means for detecting signal properties of a pulsed signal emitted by a bioimpedance sensor of an implanted device, means for analyzing the detected signal properties to determine properties of an impedance sensing signal, and means for generating the impedance sensing signal that produces substantially no interference with the pulsed signal of the implanted device.

In accordance with still another aspect of the present invention, there is provided a cardiorespiratory monitor that includes a first pair of electrodes adapted to be coupled in spaced apart relation to one another on a patient's body. A second pair of electrodes is adapted to be coupled in spaced apart relation to one another on the patient's body. A voltage sensor is coupled to the first pair of electrodes to detect pulsed voltage signals within the patient's body generated by a device implanted in the patient's body. A processor is coupled to the voltage sensor. The processor receives the detected pulsed voltage signals and determines a frequency and timing of the detected pulsed voltage signals. The processor generates a timing signal correlative to the frequency and timing of the detected pulsed voltage signals. An impedance sensor control circuit is coupled to receive the timing signal from the processor. The impedance sensor circuit generates an impedance sensing signal correlative to the timing signal and delivers the impedance sensing signal to one of the second pair of electrodes. The impedance sensing signal is timed to produce substantially no interference with the pulsed voltage signals generated by the implanted device.

In accordance with yet another aspect of the present invention, there is provided a cardiorespiratory monitor that includes a detector adapted to detect a pulsed voltage signal generated by the implantable device. A processor is coupled to the detector. The processor receives the detected pulsed voltage signal and determines a frequency and timing of the detected pulsed voltage signal. The processor generates a timing signal correlative to the frequency and timing of the detected pulsed voltage signal. An impedance sensor control circuit is coupled to receive the timing signal from the processor. The impedance sensor circuit generates an impedance sensing signal correlative to the timing signal. The impedance sensing signal is timed to produce substantially no interference with the pulsed voltage signal generated by the implanted device. A first pair of electrodes is adapted to be coupled in spaced apart relation to one another on a patient's body. The first pair of electrodes delivers the impedance sensing signal to the patient's body. A second pair of electrodes is adapted to be coupled in spaced apart relation to one another on the patient's body. The second pair of electrodes detects the impedance sensing signal delivered by the first pair of electrodes and delivers the detected impedance sensing signal to the processor. The processor generates at least one signal correlative to the detected impedance sensing signal.

BRIEF DESCRIPTION OF THE DRAWINGS

The foregoing and other advantages of the invention will become apparent upon reading the following detailed description and upon reference to the drawings in which.

DESCRIPTION OF THE SPECIFIC EMBODIMENTS

The present invention is directed to a cardiorespiratory monitor with synchronized bioimpedance sensing. In other words, the monitor carries out its impedance measurements in synchronism with the impedance measurements being taken by an implanted device. Generally speaking, the monitor determines the frequency and timing of the micropulses emitted by the implantable device's impedance sensor and uses this information to time the delivery of its own impedance sensing signal so as not to coincide with the impedance sensing signal delivered by the implanted device. Because of this lack of coincidence, the use of the monitor on the patient does not result in cross-interference with the implanted device.

Before discussing the detailed operation of the embodiment of such a monitor, however, it is believed to be important to understand the manner in which a typical implantable device, such as a pacemaker, operates. Therefore, a typical implantable pacemaker is described below as an example of an implantable device, with the understanding that the present invention, as defined by the claims, may also be useful in situations involving other types of implantable devices.

Figure 1:
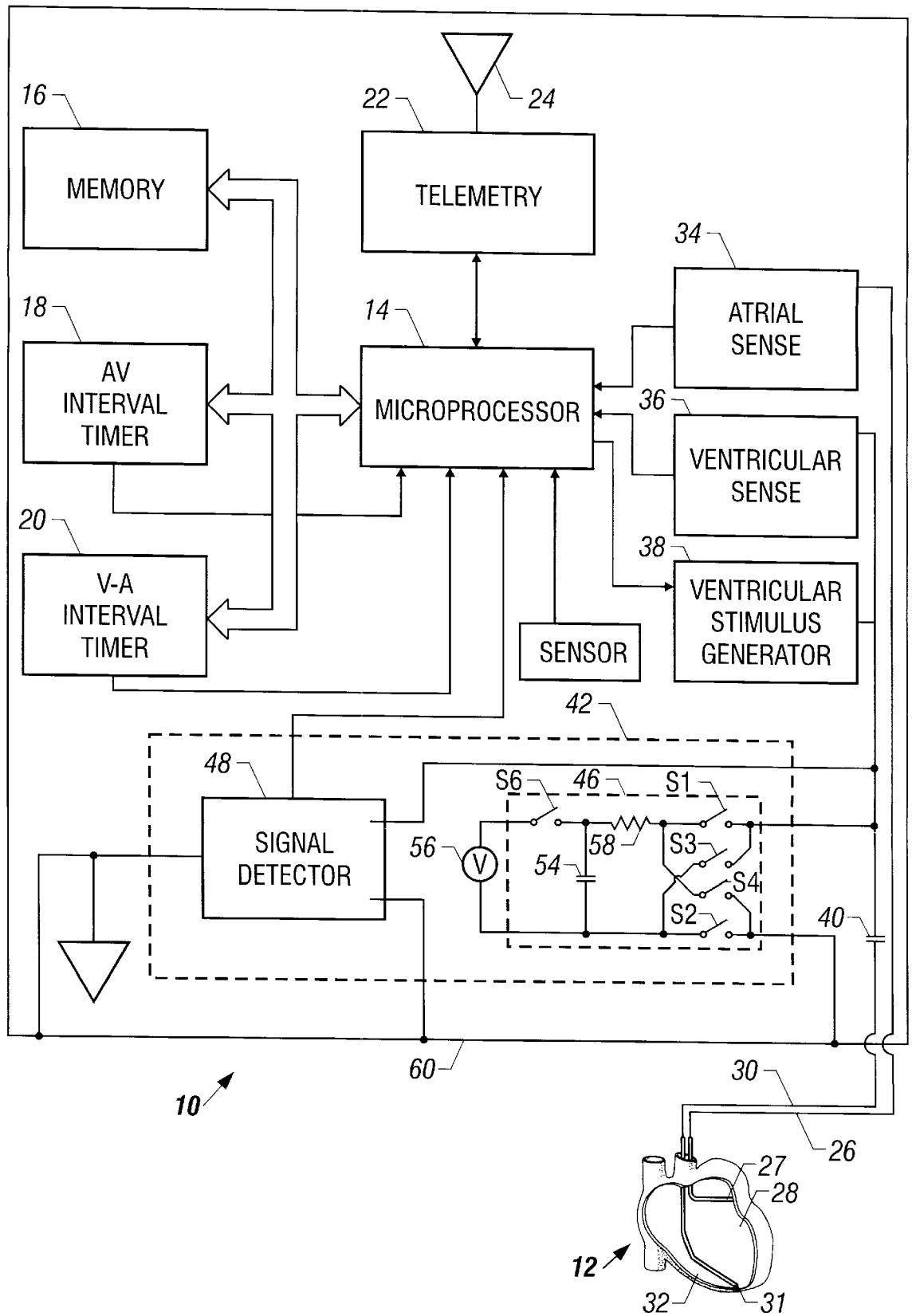
FIG. 1 illustrates a block diagram of an exemplary rate adaptive pacemaker that includes a pulse-based bioimpedance sensor.

Turning now to the drawings, and referring initially to FIG. 1, an implantable pacemaker having an impedance sensor is illustrated in schematic fashion and generally designated with a reference numeral 10. The pacemaker 10 is illustrated as being connected to a human heart 12. The pacemaker 10 includes a microprocessor 14 that executes various control programs to regulate the action of the pacemaker. The microprocessor 14 is connected to additional memory 16 for the storage of programs and data as may be needed. As is known in the art, one or more internal clocks may be provided to permit timing of various events. For example, an A-V interval timer 18 and a V-A interval timer 20 may be provided. The microprocessor is coupled to a telemetry circuit 22 so that the pacemaker 10 may communicate across an antenna 24 to an external programmer (not shown). The telemetry circuit 22 permits an attending physician to obtain data and information from the pacemaker and to control the pacemaker to set various selectable parameters, as known in the art.

The pacemaker 10 is connected to the heart 12 through a first lead 26 to an electrode 27 in the atrium 28 and through a second lead 30 to an electrode 31 in the ventricle 32. An indifferent electrode is provided to complete the electrical circuit through the body. In the illustrated embodiment, the outer casing of the pacemaker 10, typically called a can 60, serves as the indifferent electrode. Atrial sensing, through an atrial sense circuit 34, and ventricular sensing, through a ventricular sense circuit 36, provide information to the microprocessor 14 concerning the condition and responsiveness of the heart 12. The microprocessor 14 uses this information to control the delivery of pacing pulses that are provided to the ventricle from a ventricular stimulus generator 38 through a coupling capacitor 40 in a conventional fashion.

To control the pulse rate of the ventricular stimulus generator 38, the microprocessor 14 acquires information on the condition of the heart 12 through an impedance circuit 42. The impedance circuit 42 detects changes in impedance primarily related to the physical shape of the heart as it beats and pumps blood. This information can be used to derive a measure of the stroke volume, ejection fraction, or end diastolic volume of the heart. Furthermore, the shape of the impedance waveform can provide information on other cardiac timing parameters, such as isovolumetric contraction time, pre-ejection period, and so on.

The impedance circuit 42 includes a signal injector 46, which generates an impedance sensing signal and delivers it to the patient, and a signal detector 48, which detects the impedance sensing signal in the patient. Because it is the pulsed signal generated by the signal injector 46 that is of primary concern in this disclosure, the signal injector 46 is discussed in some detail herein. Although the cardiorespiratory monitor described below may be useful with a variety of implanted devices that produce pulsed signals, this particular signal injector produces biphasic current pulses. The use of a balanced biphasic current pulse has the advantage that no net charge is transferred across the electrodes. This reduces electrode deposition and corrosion for greater biocompatability.

Figure 2:
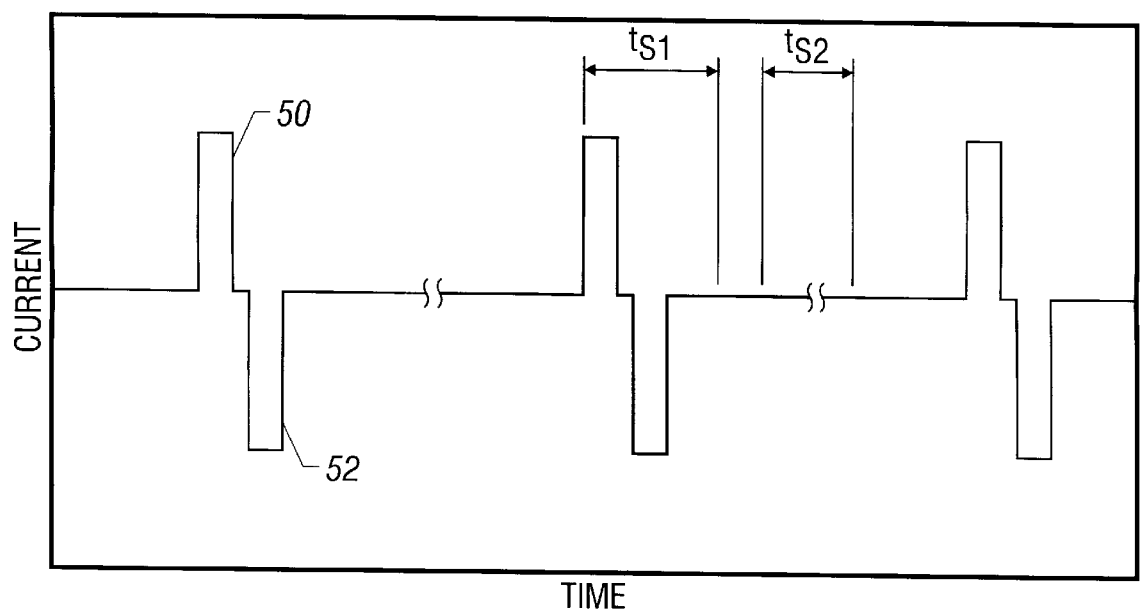
FIG. 2 illustrates a graph of a series of biphasic pulses generated by the rate adaptive pacemaker of FIG. 1.

As illustrated in FIG. 2, the biphasic signal injector 46 produces short, essentially symmetrical biphasic constant current pulses to detect the varying impedance of the heart 12. Each pulse typically has a duration of 1 to 50 microseconds and an amplitude of 0.1 to 2 milliamperes. The pulse pairs are typically produced at a frequency of about 100 Hz, but they may be produced from about 2 Hz to several hundred hertz. The resulting detected voltage across the heart valve will be on the order of 50–1000 mV.

The two pulses forming a biphasic pulse pair are substantially similar in duration and amplitude with polarity being reversed. Typically, differences in magnitude and duration between a first pulse 50 and a second pulse 52 are no more than plus or minus ten percent. In fact, pulse amplitude is usually on the order of less than 0.1% variation. The symmetrical nature of the pulses permits the impedance effect associated with each pulse to be additively combined, thus doubling the apparent magnitude of impedance change, while eliminating other effects.

The signal injector 46 includes a storage capacitor 54 that is connected to a voltage source 56 through a switch S6. The switch S6, and all of the other switches described herein, are typically controlled by the microprocessor 14. The switch S6 is closed to connect the capacitor 54 to the voltage source 56, charging the capacitor. A large resistor 58 is connected between the capacitor 54 and the switches S1, S2, S3, and S4. The resistor 58 is large enough to be the dominant impedance in the circuit, effectively creating a constant current source. Consequently, since the voltage on capacitor 54 is known, and since the effective impedance may be approximated by the impedance of the resistor 58, the current flowing through the switches S1, S2, S3, S4 into and through the heart may be determined.

To produce the first pulse 50, the switches S1 and S2 are closed while the switches S3 and S4 remain open. This connects a first side of the capacitor 54 and the resistor 58 through the switch S1 to the lead 30 and the electrode 31, and simultaneously connects a second side of the capacitor 54 through the switch S2 to the can 60. After a selected duration, for example five microseconds, the microprocessor 14 opens the switches S1 and S2 and closes the switches S3 and S4. This connects a first side of capacitor 54 and the resistor 58 through the switch S4 to the can 60, and also connects the second side of the capacitor 54 through the switch S3 to the lead 30 and the electrode 31, thus reversing the polarity of the current pulse being applied.

The voltages associated with the pulses emitted by the signal injector 46 are detected by the signal detector 48. Typically, the signal detector 48 samples the injected signal during signal injection and also for a short time thereafter, as illustrated by the sampling interval $t_{s1}$ in FIG. 2. Although the signal detector 48 may take a variety of different forms and operate in a variety of different manners, one particular embodiment and method of operation is described in U.S. Pat. No. 5,507,785. However, because it is the manner in which an implanted device generates voltage pulses for impedance sensing, rather than the manner in which the implanted device senses and calculates impedance signals, that is useful in understanding the cardiorespiratory device disclosed herein, further discussion of the operation of the signal detector 48 is omitted from this disclosure.

Figure 3:
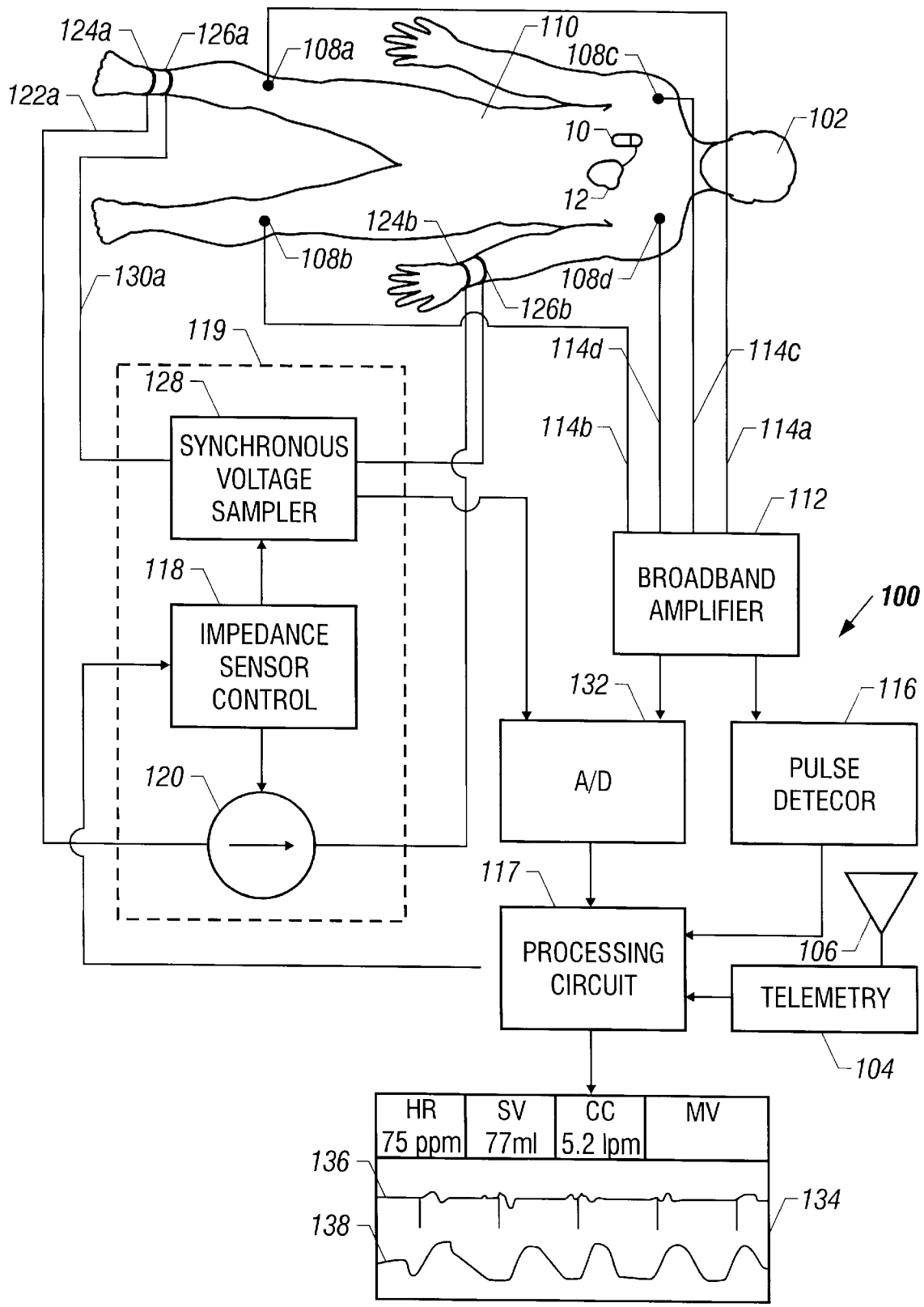
FIG. 3 illustrates a block diagram of a cardiorespiratory monitor with synchronized bioimpedance sensing in accordance with the present invention.

An exemplary cardiorespiratory monitor having synchronized bioimpedance sensing is illustrated in FIG. 3 and designated by reference numeral 100. Generally speaking, the monitor 100 first attempts to detect the pulses emitted by the impedance sensor of the implantable device 10, which is illustrated, in this embodiment, as a pacemaker coupled to the patient's heart 12. Depending upon the circumstances, various methods may be used to detect these pulses. As one example, the monitor 100 may be provided with a telemetry circuit 104 that is associated with an antenna 106. In fact, the monitor 100 may be part of a programmer for implantable cardiac stimulators that includes such a telemetry circuit. In any event, the telemetry circuit 104 may communicate with the telemetry circuit 22 of the implanted device 10, whereby the actual timing of the current pulses generated by the implantable device's impedance sensor, along with any other pertinent information, may be transmitted to the monitor 100. The telemetry circuit 104 is coupled to a processing circuit 106, which may include a microprocessor, RAM, ROM, I/O, and any other appropriate circuitry.

Alternatively, the monitor 100 may include one or more electrodes for detecting the pulses emitted by the implantable device's impedance sensor. In this embodiment, four electrodes 108A, 108B, 108C, and 108D are coupled to the patient's body 102. Two of the electrodes 108A and 108B are coupled at one end of the thorax 110, and the other two electrodes 108C and 108D are coupled at the other end of the thorax 110. The electrodes 108A, 108B, 108C, and 108D are coupled to a broadband amplifier 112 by respective leads 114A, 114B, 114C, and 114D. The broadband amplifier 112 amplifies the low-amplitude electrical signals detected by the electrodes 108A, 108B, 108C, and 108D and delivers these amplified signals to a pulse detector 116. The pulse detector 116 is preferably an AC-coupled comparator, which captures the beginning and end of each pulse generated by the implantable device 10 which was detected by the electrodes 108A, 108B, 108C, and 108D. Like the telemetry circuit 104 previously discussed, the pulse detector 116 delivers these timing signals to the processing circuit 117 for evaluation.

Once the montior 100 has detected the pulses emitted from the implanted device 10, the processing circuit 117 analyzes the detected pulses to determine certain parameters of these pulses that the monitor 100 may use in generating its own impedance sensing signal. For instance, the processing circuit 117 may determine the frequency, timing, and duration of the detected pulses. Based on these parameters, the processing circuit 117 calculates an appropriate sampling interval. In this embodiment, this sampling interval $t_{s2}$ resides between the successive pulses emitted by the implanted device 10, as illustrated in FIG. 2. During this sampling interval, the monitor 100 may carry out its current injection and voltage sampling phases. Because the current injection and voltage sampling phases of the monitor occur during a period in which the implanted device 10 is carrying out no impedance sensing, i.e., the monitor 100 is operating in synchronism with the impedance sensing of the implanted device, neither the impedance sensing of the monitor 100 nor of the implanted device 10 interferes with the impedance sensing of the other.

To initiate the monitors impedance sensing function, the processing circuit 117 delivers the appropriate timing signals to an impedance sensor control 118 which is part of an injection and sampling circuit 119. Based on these timing signals, the impedance sensor control 118, which is usually a simple state machine that activates the injector's switches and times the voltage sampler, develops control signals for injecting current pulses into the patient 102. These control signals are delivered, in this embodiment, to a current source, such as the illustrated biphasic current source 120. The biphasic current source 120 delivers biphasic current pulses to the patient 102 via the leads 122A and 122B. The leads 122A and 122B are coupled to electrodes 124A and 124B, respectively, which are coupled to the patient's leg and arm, respectively. It will be readily understood that the electrodes 124A and 124B are coupled to the patient's extremities in order to close a current path that passes through the thorax 110 of the patient 102 so that the bioimpedance measurements taken by the monitor 100 relate to the operation of the patient's heart 12. Of course, it should also be understood that thoracic impedance may also be measured with the electrodes 124A and 124B positioned at different locations on the body of the patient 102, e.g., the electrode 124A may be positioned near the patient's chest, and the electrode 124B may be positioned near the patient's neck.

To monitor the pulsed signal injected into the patient's body 102 by the biphasic current source 120, electrodes 126A and 126B are coupled to the patient's body 102 at a location near the electrodes 124A and 124B, respectively. The electrodes 126A and 126B are coupled to a synchronous voltage sampler 128 via the leads 130A and 130B, respectively. The synchronous voltage sampler 128 samples the voltage signals in the patient in synchronism with the pulsed signal delivered by the monitor 100. In other words, it samples the voltage signals in the patient during the delivery of each pulse produced by the current source 120 and, advantageously, for a short time thereafter. Because this sampling takes place during the sampling interval, the voltage remnants related to the implanted device are no longer present, so this sampled voltage relates to the signal injected by the monitor 100. Thus, the sampled voltage provides a better indication of bioimpedance than currently known non-synchronous systems, without undesirable cross-interference.

The synchronous voltage sampler 128 delivers the sampled impedance signal to an analog-to-digital converter 132. The analog-to-digital converter 132 also receives and ECG signal, which is sensed by the electrodes 108A, 108B, 108C, and 108D and amplified by the broadband amplifier 112. The analog-to-digital converter 132 converts each of these signals to a digital format that is appropriate for the processing circuit 117.

The processing circuit 117 processes the impedance signal and the ECG signal in a conventional manner to produce indications of cardiorespiratory function. These indications may be presented in numerical and/or graphical form on a screen 134 that is part of the monitor 100. For example, the screen 134 may display numerical values of heart rate (HR), stroke volume (SV), cardiac output (CO), and minute ventilation (MV), along with graphical representations of the ECG signal 136 and the impedance signal 138.

As discussed above, the monitor 100 may be coupled to a patient who has an implanted device that uses a bioimpedance sensor, or the like, without producing cross-interference that could cause the implanted device to operate in a less than ideal manner and cause the cardiorespiratory monitor to generate an inaccurate bioimpedance reading. This is particularly advantageous in certain emergency situations when emergency personnel may not be able to determine whether a patient has such an implanted device. Accordingly, as compared with conventional cardiorespiratory monitors, the monitor 100 may be more advantageous for the diagnosis and treatment of cardiac dysfunction.

However, the monitor 100 is more useful than conventional monitors in other ways as well. For example, it may be used to calibrate an implanted bioimpedance sensor more accurately than conventional techniques. Specifically, the monitor 100 may be coupled to a patient having an implanted bioimpedance sensor. Once the monitor 100 has detected the pulses emitted by the implanted electrode and synchronized its own bioimpedance sensor accordingly, the monitor 100 is able to generate an accurate reading of the patient's particular bioimpedance. Unlike the bioimpedance sensed by conventional monitors, the bioimpedance sensed by the monitor 100 is not distorted with signals produced by the impedance sensing signals emitted by the implanted device. Therefore, this more accurate measure of the patient's bioimpedance may be used to calibrate the bioimpedance sensor of the implanted device. This measurement may be communicated to the implanted device via the telemetry circuit 104.

To this point in the discussion, both the implanted device 10 and the monitor 100 have been described as emitting a pulsed signal that is used to sense the bioimpedance of a patient. However, as stated in the discussion regarding the related art, high frequency AC signals may also be used to sense bioimpedance. While implanted devices typically use pulse-based methods, as described above, due to the power savings involved, external cardiorespiratory monitors are not encumbered with this concern. Accordingly, another problem relates to cross-interference produced by a cardiorespiratory monitor that uses a high frequency AC signal for bioimpedance sensing.

To address this problem, an alternate embodiment of the monitor 100 is suggested. In this alternate embodiment, the monitor 100 detects and evaluates the pulsed signal emitted from the bioimpedance sensor of the implanted device in essentially the same manner as described above. However, instead of generating a timing signal useful for a pulsed injection signal, the processing circuit 117 generates a timing signal useful for a high frequency AC injection signal. Specifically, the timing of the high frequency AC injection signal is set so that the zero crossing of the high frequency AC injection signal corresponds with the pulse emitted by the bioimpedance sensor of the implanted device. In this manner, little or no power is generated by the bioimpedance sensing of the monitor 100 during the periods in which the implanted device is sensing bioimpedance.

The processing circuit 117 delivers this timing signal to the injection and sampling circuit 119, which includes circuits for injecting and sampling the high frequency AC signals rather than the circuits for injecting and sampling the pulsed signals described above. Although the implanted device will produce pulses during periods in which the monitor 100 is sensing impedance, the monitor may be programmed to ignore these pulses. Thus, the monitor 100 not only produces substantially no interference with the signal generated by the implanted device, it also generates an accurate reading of bioimpedance even in patients having an implanted bioimpedance sensor.

While the invention may be susceptible to various modifications and alternative forms, specific embodiments have been shown by way of example in the drawings and described in detail herein. However, it should be understood that the invention is not intended to be limited to the particular forms disclosed. Rather, the invention is to cover all modifications, equivalents, and alternatives falling within the spirit and scope of the invention as defined by the following appended claims.

What is claimed is:

1. A cardiorespiratory measurement device comprising:
   means for determining timing of an impedance test signal generated by an implanted device;
   means for generating a bioimpedance sensing signal, and
   means for correlating generation of said bioimpedance sensing signal so that generation of said bioimpedance sensing signal produces substantially no interference with the signal of the implanted device.

2. The device, as set forth in claim 1, wherein the determining means comprises means for detecting pulses generated by the implanted device.

3. The device, as set forth in claim 1, wherein the determining means comprises means for communicating with the implanted device.

4. The device, as set forth in claim 1, wherein the generating means comprises means for generating a pulsed bioimpedance sensing signal.

5. The device, as set forth in claim 1, wherein the generating means comprises means for generating a high frequency AC bioimpedance sensing signal.

6. A cardiorespiratory measurement device comprising:
   means for detecting signal properties of a pulsed signal emitted by a bioimpedance sensor of an implanted device;
   means for analyzing the detected signal properties to determine properties of an impedance sensing signal;
   means for generating the impedance sensing signal that produces substantially no interference with the pulsed signal of the implanted device.

7. The device, as set forth in claim 6, wherein the detecting means comprises means for communicating with the implanted device.

8. The device, as set forth in claim 6, wherein the analyzing means comprises a processing circuit.

9. The device, as set forth in claim 6, wherein the generating means comprises means for generating a pulsed impedance sensing signal.

10. The device, as set forth in claim 6, wherein the generating means comprises means for generating a high frequency AC impedance sensing signal.

11. A cardiorespiratory monitor comprising:
    a first pair of electrodes adapted to be coupled in spaced apart relation to one another on a patient's body;
    a second pair of electrodes adapted to be coupled in spaced apart relation to one another on the patient's body;
    a voltage sensor coupled to the first pair of electrodes to detect pulsed voltage signals within the patient's body generated by a device implanted in the patient's body;
    a processor coupled to the voltage sensor, the processor receiving the detected pulsed voltage signals and having means for determining a frequency and timing of the detected pulsed voltage signals, and means for generating a timing signal correlative to the frequency and timing of the detected pulsed voltage signals; and
    an impedance sensor control circuit coupled to receive the timing signal from the processor, the impedance sensor control circuit having means for generating an impedance sensing signal correlative to the timing signal and delivering the impedance sensing signal to one of the second pair of electrodes, and means for timing the generation of the impedance sensing signal to produce substantially no interference with the pulsed voltage signals generated by the implanted device.

12. The monitor, as set forth in claim 11, wherein the impedance sensor control circuit comprises a current source coupled to deliver a pulsed impedance sensing signal to one of the second pair of electrodes.

13. The monitor, as set forth in claim 11, wherein the impedance sensor control circuit comprises a current source coupled to deliver a high frequency AC impedance sensing signal to one of the second pair of electrodes.

14. The monitor, as set forth in claim 11, further comprising a voltage sampling device coupled to the impedance sensor control circuit, the voltage sampling device detecting the impedance sensing signal and delivering the detected impedance sensing signal to the processor, the processor generating at least one signal correlative to the detected impedance sensing signal.

15. A cardiorespiratory monitor comprising:
    a first telemetry circuit adapted to communicate with a second telemetry circuit of an implantable device to receive a synchronization signal correlative to a pulsed voltage signal generated by the implantable device;
    a processor coupled to the first telemetry circuit, the processor receiving the synchronization signal and determining a frequency and timing of the pulsed voltage signal, and the processor having means for generating a timing signal correlative to the frequency and timing of the pulsed voltage signal;
    an impedance sensor control circuit coupled to receive the timing signal from the processor, the impedance sensor control circuit having means for generating an impedance sensing signal correlative to the timing signal, and means for timing the generation of the impedance sensing signal to produce substantially no interference with the pulsed voltage signal generated by the implanted device;
    a first pair of electrodes adapted to be coupled in spaced apart relation to one another on a patient's body, the first pair of electrodes delivering the impedance sensing signal to the patient's body; and
    a second pair of electrodes adapted to be coupled in spaced apart relation to one another on the patient's body, the second pair of electrodes detecting the impedance sensing signal delivered by the first pair of electrodes and delivering the detected impedance sensing signal to the processor, the processor generating at least one signal correlative to the detected impedance sensing signal.

16. The monitor, as set forth in claim 15, wherein the impedance sensor control circuit generates a pulsed signal.

17. The monitor, as set forth in claim 15, wherein the impedance sensor control circuit generates a high frequency AC signal.

18. The monitor, as set forth in claim 15, wherein the second pair of electrodes delivers the detected impedance sensing signal to a voltage sampler that delivers the impedance sensing signal to the processor.

19. The monitor, as set forth in claim 18, wherein the voltage sampler operates synchronously with the impedance sensor control circuit.

20. The monitor, as set forth in claim 15, wherein the first telemetry circuit delivers the at least one signal correlative to the detected impedance sensing signal to the second telemetry circuit.

21. A cardiorespiratory monitor comprising:
a detector adapted to detect a pulsed voltage signal generated by the implantable device;
a processor coupled to the detector, the processor receiving the detected pulsed voltage signal and having means for determining a frequency and timing of the detected pulsed voltage signal, and means for generating a timing signal correlative to the frequency and timing of the detected pulsed voltage signal;
an impedance sensor control circuit coupled to receive the timing signal from the processor, the impedance sensor control circuit having means for generating an impedance sensing signal correlative to the timing signal, and means for timing the generation of the impedance sensing signal to produce substantially no interference with the pulsed voltage signal generated by the implanted device;
a first pair of electrodes adapted to be coupled in spaced apart relation to one another on a patient's body, the first pair of electrodes delivering the impedance sensing signal to the patient's body; and
a second pair of electrodes adapted to be coupled in spaced apart relation to one another on the patient's body, the second pair of electrodes detecting the impedance sensing signal delivered by the first pair of electrodes and delivering the detected impedance sensing signal to the processor, the processor generating at least one signal correlative to the detected impedance sensing signal.

22. The monitor, as set forth in claim 21, wherein the detector comprises a pulse detector.

23. The monitor, as set forth in claim 21, wherein the detector comprises a telemetry circuit.

24. The monitor, as set forth in claim 21, wherein the impedance sensor control circuit generates a pulsed signal.

25. The monitor, as set forth in claim 21, wherein the impedance sensor control circuit generates a high frequency AC signal.

26. The monitor, as set forth in claim 21, wherein the second pair of electrodes delivers the detected impedance sensing signal to a voltage sampler that delivers the impedance sensing signal to the processor.

27. The monitor, as set forth in claim 26, wherein the voltage sampler operates synchronously with the impedance sensor control circuit.

28. A device for calibrating a bioimpedance sensor of an implanted device, the device comprising:

a first telemetry circuit adapted to communicate with a second telemetry circuit of the implanted device to receive a synchronization signal correlative to a pulsed voltage signal generated by the implanted device;
a processor coupled to the first telemetry circuit, the processor receiving the synchronization signal from the first telemetry circuit and having means for determining a frequency and timing of the pulsed voltage signal, and means for generating a timing signal correlative to the frequency and timing of the pulsed voltage signal;
an impedance sensor control circuit coupled to receive the timing signal from the processor, the impedance sensor control circuit having means for generating an impedance sensing signal correlative to the timing signal, and means for timing the generation of the impedance sensing signal to produce substantially no interference with the pulsed voltage signal generated by the implanted device;
a first pair of electrodes adapted to be coupled in spaced apart relation to one another on a patient's body, the first pair of electrodes delivering the impedance sensing signal to the patient's body; and
a second pair of electrodes adapted to be coupled in spaced apart relation to one another on the patient's body, the second pair of electrodes detecting the impedance sensing signal delivered by the first pair of electrodes and delivering the detected impedance sensing signal to the processor, the processor generating a calibration signal correlative to the detected impedance sensing signal and delivering the calibration signal to the first telemetry circuit for delivery to the second telemetry circuit, the calibration signal being usable by the implanted device to calibrate the bioimpedance sensor of the implanted device.

29. The device, as set forth in claim 28, wherein the impedance sensor control circuit generates a pulsed signal.

30. The device, as set forth in claim 28, wherein the impedance sensor control circuit generates a high frequency AC signal.

31. The device, as set forth in claim 28, wherein the second pair of electrodes delivers the detected impedance sensing signal to a voltage sampler that delivers the impedance sensing signal to the processor.

32. The device, as set forth in claim 31, wherein the voltage sampler operates synchronously with the impedance sensor control circuit.

* * * * *